United States Patent [19]

Vlasblom

[11] Patent Number: 5,698,475
[45] Date of Patent: Dec. 16, 1997

[54] CLEANER IMPREGNATED TOWEL

[75] Inventor: Jack T. Vlasblom, Dunedin, Fla.

[73] Assignee: Dotolo Research Corporation, Largo, Fla.

[21] Appl. No.: 654,174

[22] Filed: May 28, 1996

[51] Int. Cl.$^6$ .................................................. B32B 9/00
[52] U.S. Cl. ................... 442/59; 428/279; 428/288; 428/290; 428/301; 428/304.4; 428/305.5; 428/311.5; 428/403; 428/905
[58] Field of Search .................... 428/279, 305.5, 428/905, 288, 195, 290, 403, 301, 235, 304.4, 311.5

[56] References Cited

U.S. PATENT DOCUMENTS

| | | |
|---|---|---|
| 4,511,495 | 4/1985 | Melville . |
| 4,938,888 | 7/1990 | Kiefer et al. . |
| 5,300,238 | 4/1994 | Lin et al. . |
| 5,372,751 | 12/1994 | Rys-Cicciari ............ 252/554 |
| 5,512,199 | 4/1996 | Khan et al. ............ 252/106 |

*Primary Examiner*—Patrick Ryan
*Assistant Examiner*—Abraham Bahta
*Attorney, Agent, or Firm*—Donald R. Fraser

[57] ABSTRACT

A cleaner impregnated towel comprises a flexible, porous substrate, a cleaner comprising a salt of the coconut fatty acid ester of isethionic acid, and optionally an antimicrobial compound comprising 5-chloro-2-(2,4-dichlorophenoxy) phenol and parachlorometaxylenol, impregnated within the substrate.

18 Claims, No Drawings

CLEANER IMPREGNATED TOWEL

FIELD OF THE INVENTION

This invention relates generally to a cleaner impregnated towel. More particularly, the invention is directed to a non-woven or woven substrate that is impregnated with a cleaner useful for cleansing the skin of a human or an animal.

BACKGROUND OF THE INVENTION

Cleaners for cleansing the skin of humans and animals are known in the art. Likewise, it is known to combine premeasured amounts of cleaners with articles such as pouches or flexible carrier sheets.

U.S. Pat. No. 4,938,888 to Kiefer et al. discloses a detergent sheet, comprising an alkyl polyglycoside and a detergency builder impregnated into a flexible substrate. The detergent formulation disclosed in Kiefer et al., however, is harsh and unsuitable for prolonged contact with human or animal skin. Generally, the detergent sheets disclosed in the prior art contain detergents or other ingredients which irritate the skin.

It would be desirable to develop a cleaner impregnated towel which is mild in contact with human and animal skin, delivers copious quantities of stable foam, and is cost effective.

SUMMARY OF THE INVENTION

Accordant with the present invention, a cleaner impregnated towel having desired qualities surprisingly has been discovered. The inventive cleaner impregnated towel comprises:

a flexible, porous substrate; and a cleaner impregnated into said substrate, said cleaner comprising a salt of the coconut fatty acid ester of isethionic acid.

The cleaner impregnated towel according to the present invention is particularly useful for cleansing the skin of humans and animals.

Further objects and advantages of this invention will be apparent from the following description and appended claims.

DETAILED BRIEF DESCRIPTION OF THE DRAWINGS

The present invention is directed to a cleaner impregnated towel. The towel may be any conventional flexible, porous substrate, and the cleaner comprises a salt of the coconut fatty acid ester of isethionic acid. Alternatively, the cleaner also includes an antimicrobial agent comprising a mixture of 5-chloro-2-(2,4-dichlorophenoxy) phenol and parachlorometaxylenol. In the present invention, 5-chloro-2-(2,4-dichlorophenoxy) phenol is the technical name for the compound designated under I.U.P.A.C. as 2, 2, 4'-trichloro-2'-hydroxydiphenyl ether.

The flexible, porous substrate may comprise any monolithic flexible, porous material including, but not necessarily limited to a non-woven or woven textile cloth or mat, a sponge material, paper, or the like. A preferred non-woven substrate would generally comprise adhesively bonded fibrous or filamentous materials having a web or carded fiber structure, or a mat in which the fibers are distributed either in a random fashion or in a substantially aligned manner. The fibers or filaments generally comprise natural materials, e.g., wood, silk, jute, hemp, cotton, linen, and the like, or synthetic materials, e.g., polyolefins, polyesters, rayon, cellulose ester, polyvinyl derivatives, polyamides, and the like, as well as combinations thereof.

The thickness of the substrate may vary over wide limits, and is generally of a thickness that will conveniently retain within its porous structure a quantity of an impregnated cleaner suitable for cleaning the skin of humans or animals. Typically, the fibers or filaments have a Denier from about 1.5 to about 5, and are from about 5mm to about 50mm in length. Preferably, the fibers are at least partially randomly placed in the substrate and are adhesively bonded together with a substantially hydrophobic binder. A preferred flexible, porous substrate is available from Dexter Nonwoven, Inc., Windsor Locks, CN, under the product designation HYDRASPUN.

The present invention contemplates the impregnation of a dry cleaner compound within the substrate. This effectively reduces the shipping weight of the product by eliminating the liquid "bulk" therefrom. Thus, the present invention provides a commercial advantage over most prior art detergent sheets which incorporate a liquid soap in the pre-treated towels. The reduced shipping weight of the cleaner impregnated towels of the present invention results in a corresponding reduction in the transportation cost for the final product. The "dry towel" according to the present invention eliminates the need for a messy soap bar, and reduces the likelihood of the growth of opportunistic microorganisms on the impregnated cleaner compound, because of the absence of water. The cleaner chosen must be capable of being solubilized in a solvent system, for application to the substrate, followed by evaporation of the solvent, without the cleaner itself being chemically altered. Additionally, the cleaner or "soap" must be compatible with other adjuvants, particularly antimicrobial additives, since an alternative embodiment of the cleaner impregnated towel according to the present invention includes an antimicrobial compound and is particularly desirable for use in hospitals, day care centers, nursing homes, and similar institutions. Finally, the cleaner must be mild, capable of generating a large amount of stable foam, and must be cost effective.

The cleaner for use according to the present invention comprises a salt of the coconut fatty acid ester of isethionic acid, and conforms generally to the formula:

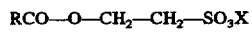

$$RCO-O-CH_2-CH_2-SO_3X$$

wherein RCO— represents fatty acids derived from coconut oil and X is the ion to which the salt is bonded. Preferably, the salt comprises the sodium, potassium, or ammonium salt of the coconut fatty acid ester of isethionic acid, or any mixture thereof. A most preferred salt comprises sodium cocoyl isethionate, having CAS numbers 61789-32-0 and 58969-27-0. This syndet cleaner offers many advantages over true soaps, e.g., it is easier to fragrance, it is milder to the skin of humans and animals, it exhibits high foam production, it is unlikely to produce allergic dermatoses, and it is capable of being solubilized for deposition onto and impregnation into a flexible, porous substrate without altering its chemical structure. Moreover, this cleaner is unaffected by hard or mineralized water and therefore does not cause a "bathtub ring" of an insoluble mineral residue. Salts of the coconut fatty acid ester of isethionic acid are well-known in the art. Sodium cocoyl isethionate may be obtained commercially from PPG Industries, Inc., Gurnee, IL under the product designation JORDAPON.

In an alternative embodiment of the cleaner impregnated towel according to the present invention, an antimicrobial compound is added to the cleaner before its impregnation into the substrate. The antimicrobial compound comprises a mixture of 5-chloro-2-(2,4-dichlorophenoxy) phenol and parachlorometaxylenol. The weight ratio of antimicrobial compound relative to the salt may vary over wide limits from about 1:1 to about 1:100. Preferably, the ratio is about 1:50. Likewise, the weight ratio of 5-chloro-2-(2,4-dichlorophenoxy) phenol relative to parachlorometaxylenol in the antimicrobial compound may vary over wide limits from about 1:10 to about 10:1. Preferably, the ratio is about 1:1. The 5-chloro-2-(2,4-dichlorophenoxy) phenol is a known compound and is commercially available from Ciba Geigy Co. of Greensboro, North Carolina under the trade designation "IRGASAN DP300". The parachlorometaxylenol is likewise commercially available from Boots PLC of the United Kingdom under the trade designation "PCMX".

The cleaner impregnated towel according to the alternative embodiment of the present invention, containing the specified antimicrobial agent, is particularly suited for use in the food processing industry, hospitals, and similar institutional settings where the expense, inconvenience, and harshness of products currently on the market preclude their frequent use for hand washing which is desirable in order to preclude the spread of infectious microorganisms.

In operation a web of the flexible, porous substrate may be sprayed with the solubilized cleaner, or alternatively, the substrate web may be conveyed through a wetting vat of the solubilized cleaner. Thus, the substrate web is coated and infused with the solubilized cleaner. Thereafter, the coated web may be conveyed over a series of heated rolls within an airlocked vacuum chamber to vaporize the solvent from the substrate. The recovered solvent may then be recycled for reuse in solubilizing additional cleaner.

Suitable solvents for solubilizing the cleaner include, but are not necessarily limited to, water, methyl ethyl ketone, acetone, trichloroethylene, methanol, ethanol, and the like, as well as mixtures thereof. A preferred solvent comprises a mixture of water and methyl ethyl ketone, wherein the ratio of water to methyl ethyl ketone ranges from about 1:1 to about 1:5. Where the cleaner includes the antimicrobial compound, the salt, 5-chloro-2-(2,4-dichlorophenoxy) phenol, and parachlorometaxylenol are first mixed together, then added to the solvent. The resultant cleaner impregnated substrate web may then be cut into desired sizes to produce individual cleaner impregnated towels. Each such towel includes a fine crystalline deposit of the cleaner adhered to the fibers or filaments within the porous structure of the product. The cleaner impregnated towels of the present invention may then be activated by wetting same with water, for example, by use in a shower.

EXAMPLE I

A solution of about 40 weight % sodium cocoyl isethionate, about 30 weight % methyl ethyl ketone, and about 30 weight % water is sprayed onto a web of non-woven paper. The treated paper is thereafter heated to evaporate the methyl ethyl ketone and water, resulting in a web of non-woven paper containing a fine crystalline deposit of sodium cocoyl isethionate within the pores thereof. The web is cut to desired sized pieces, to produce cleaner impregnated towels according to the present invention.

EXAMPLE II

A solution of about 40 weight % potassium cocoyl isethionate, about 50 weight % methyl ethyl ketone, about 9 weight % water, about 0.5 weight % 5-chloro-2-(2,4-dichlorophenoxy) phenol, and about 0.5 weight % parachlorometaxylenol is sprayed onto a web of non-woven paper. The treated paper is thereafter heated to evaporate the methyl ethyl ketone and water, resulting in a web of non-woven paper containing a fine crystalline deposit of potassium cocoyl isethionate, parachlorometaxylenol, and 5-chloro-2-(2,4-dichlorophenoxy) phenol within the pores thereof. The web is thereafter cut to desired sized pieces, to produce cleaner impregnated towels according to the alternative embodiment of the present invention.

The cleaner impregnated towel described hereinabove generally has been described in terms of its broadest application to the practice of the present invention. Occasionally, however, the materials or the process conditions described may not be precisely applicable to each cleaner impregnated towel variant included within the disclosed scope. Those instances where this occurs will be readily recognized by those ordinarily skilled in the art. In all such cases, the product may be prepared and the process may successfully be performed by routine modifications to the disclosed product or process, e.g., other flexible, porous substrates may be used, or other methods of impregnating the substrate may be employed, etc., or modifications which are otherwise conventional may be made.

The invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A cleaner impregnated towel, consisting essentially of:
    a flexible, porous substrate; and
    a cleaner impregnated into said substrate, said cleaner consisting essentially of a salt of the coconut fatty acid ester of isethionic acid.

2. The cleaner impregnated towel according to claim 1, wherein the substrate is non-woven.

3. The cleaner impregnated towel according to claim 1, wherein the substrate comprises fibers selected from the group consisting of wood, silk, jute, hemp, cotton, linen, polyolefins, polyesters, rayon, cellulose ester, polyvinyl derivatives, polyamides, and combinations thereof.

4. The cleaner impregnated towel according to claim 1, wherein the substrate fibers have a Denier from about 1.5 to about 5.

5. The cleaner impregnated towel according to claim 1, wherein the substrate fibers have lengths from about 5 mm to about 50 mm.

6. The cleaner impregnated towel according to claim 1, wherein the salt comprises a salt selected from the group consisting of the sodium, potassium, and ammonium salts of the coconut fatty acid ester of isethionic acid, and mixtures thereof.

7. The cleaner impregnated towel according to claim 6, wherein the salt is sodium cocoyl isethionate.

8. A cleaner impregnated towel, consisting essentially of:
    a flexible, porous substrate;
    a cleaner impregnated into the substrate, said cleaner consisting essentially of a salt of the coconut fatty acid ester of isethionic acid; and
    an antimicrobial compound impregnated into the substrate, said antimicrobial compound consisting essentially of 5-chloro-2-(2,4-dichlorophenoxy) phenol and parachlorometaxylenol.

9. The cleaner impregnated towel according to claim 8, wherein the substrate is non-woven.

10. The cleaner impregnated towel according to claim 8, wherein the substrate comprises fibers selected from the group consisting of wood, silk, jute, hemp, cotton, linen, polyolefins, polyester, rayon, cellulose ester, polyvinyl derivatives, polyamides, and combinations thereof.

11. The cleaner impregnated towel according to claim 8, wherein the substrate fibers have a Denier from about 1.5 to about 5.

12. The cleaner impregnated towel according to claim 8, wherein the substrate fibers have lengths from about 5 mm to about 50 mm.

13. The cleaner impregnated towel according to claim 8, wherein the weight ratio of antimicrobial compound to cleaner ranges from about 1:1 to about 1:100.

14. The cleaner impregnated towel according to claim 13, wherein the ratio is about 1:50.

15. The cleaner impregnated towel according to claim 8, wherein the weight ratio of 5-chloro-2-(2,4-dichlorophenoxy) phenol to parachlorometaxylenol ranges from about 1:10 to about 10:1.

16. The cleaner impregnated towel according to claim 15, wherein the ratio is about 1:1.

17. The cleaner impregnated towel according to claim 8, wherein the salt comprises a salt selected from the group consisting of the sodium, potassium, and ammonium salts of the coconut fatty acid ester of isethionic acid, and mixtures thereof.

18. The cleaner impregnated towel according to claim 17, wherein the salt is sodium cocoyl isethionate.

* * * * *